(12) United States Patent
Tadross

(10) Patent No.: US 11,867,807 B2
(45) Date of Patent: Jan. 9, 2024

(54) SYSTEM AND METHODS FOR BEAMFORMING SOUND SPEED SELECTION

(71) Applicant: GE Precision Healthcare LLC, Milwaukee, WI (US)

(72) Inventor: Rimon Tadross, Milwaukee, WI (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 162 days.

(21) Appl. No.: 17/446,694

(22) Filed: Sep. 1, 2021

(65) Prior Publication Data

US 2023/0065683 A1   Mar. 2, 2023

(51) Int. Cl.
*G01S 15/89* (2006.01)
*G10K 11/34* (2006.01)
*A61B 8/00* (2006.01)

(52) U.S. Cl.
CPC ........ *G01S 15/8915* (2013.01); *G10K 11/341* (2013.01); *A61B 8/4483* (2013.01)

(58) Field of Classification Search
CPC ....... A61B 8/5207; A61B 8/54; A61B 8/4477; A61B 8/4483; G10K 11/341; G01S 15/8915
See application file for complete search history.

(56) References Cited

U.S. PATENT DOCUMENTS

| | | | |
|---|---|---|---|
| 5,388,461 A | 2/1995 | Rigby | |
| 5,638,820 A | 6/1997 | Chen et al. | |
| 5,910,115 A * | 6/1999 | Rigby | G01S 7/52046 600/443 |
| 5,935,070 A * | 8/1999 | Dolazza | G10K 11/346 600/443 |
| 8,784,318 B1 | 7/2014 | Napolitano et al. | |
| 8,862,409 B2 * | 10/2014 | Craddock | G01S 13/89 702/19 |

(Continued)

FOREIGN PATENT DOCUMENTS

EP   1965704 B1   11/2012

OTHER PUBLICATIONS

Rigby, K., "Systems and Methods for Beamforming Sound Speed Selection," U.S. Appl. No. 17/446,094, filed Aug. 26, 2021, 42 pages.

*Primary Examiner* — Daniel L Murphy
*Assistant Examiner* — Amie M Ndure
(74) *Attorney, Agent, or Firm* — McCoy Russell LLP

(57) ABSTRACT

Methods and systems are provided for receiving beamforming of ultrasound signals to generate ultrasound images with increased resolution. In one example, a method for an ultrasound system including a plurality of ultrasound transducers each coupled to a respective receive channel includes time-delaying a set of ultrasound receive channel signals to form a plurality of time-delayed sets of ultrasound receive channel signals, each time-delayed set of ultrasound receive channel signals time-delayed based on a different beamforming sound speed, calculating a beamforming quality metric for each receive channel and for each time-delayed set of ultrasound receive channel signals, and generating an ultrasound image from ultrasound receive channel signals selected from the plurality of time-delayed sets of ultrasound receive channel signals based on each beamforming quality metric.

23 Claims, 7 Drawing Sheets

(56) References Cited

U.S. PATENT DOCUMENTS

| | | |
|---|---|---|
| 9,901,323 B2 | 2/2018 | Napolitano et al. |
| 10,813,595 B2 | 10/2020 | Tsymbalenko et al. |
| 2004/0002695 A1* | 1/2004 | Youssefi ............. A61F 9/00817 606/5 |
| 2008/0242999 A1* | 10/2008 | Kakee ................ G01S 7/52046 600/458 |
| 2014/0066767 A1* | 3/2014 | Mammone ........... A61B 8/0825 600/443 |
| 2015/0196274 A1* | 7/2015 | Yamamoto .......... G01S 15/8997 600/442 |
| 2018/0161015 A1 | 6/2018 | Hollaender et al. |
| 2019/0130554 A1 | 5/2019 | Rothberg et al. |
| 2020/0158844 A1* | 5/2020 | Li ....................... G01S 7/52095 |
| 2023/0061869 A1* | 3/2023 | Rigby ................ G01S 7/52095 |

* cited by examiner

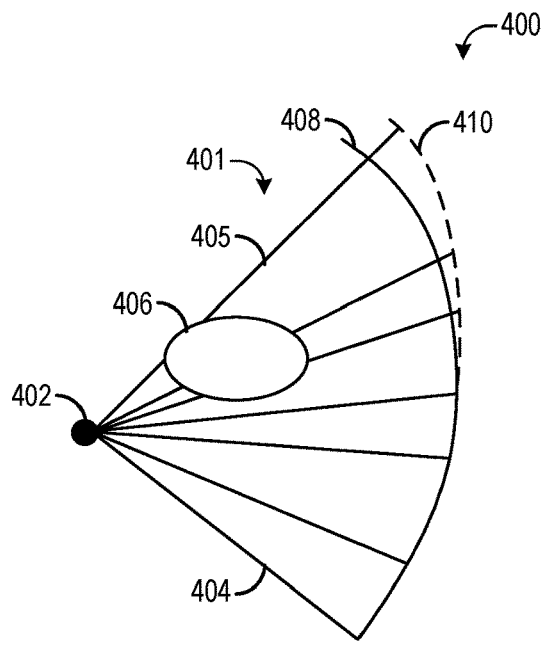
FIG. 4A
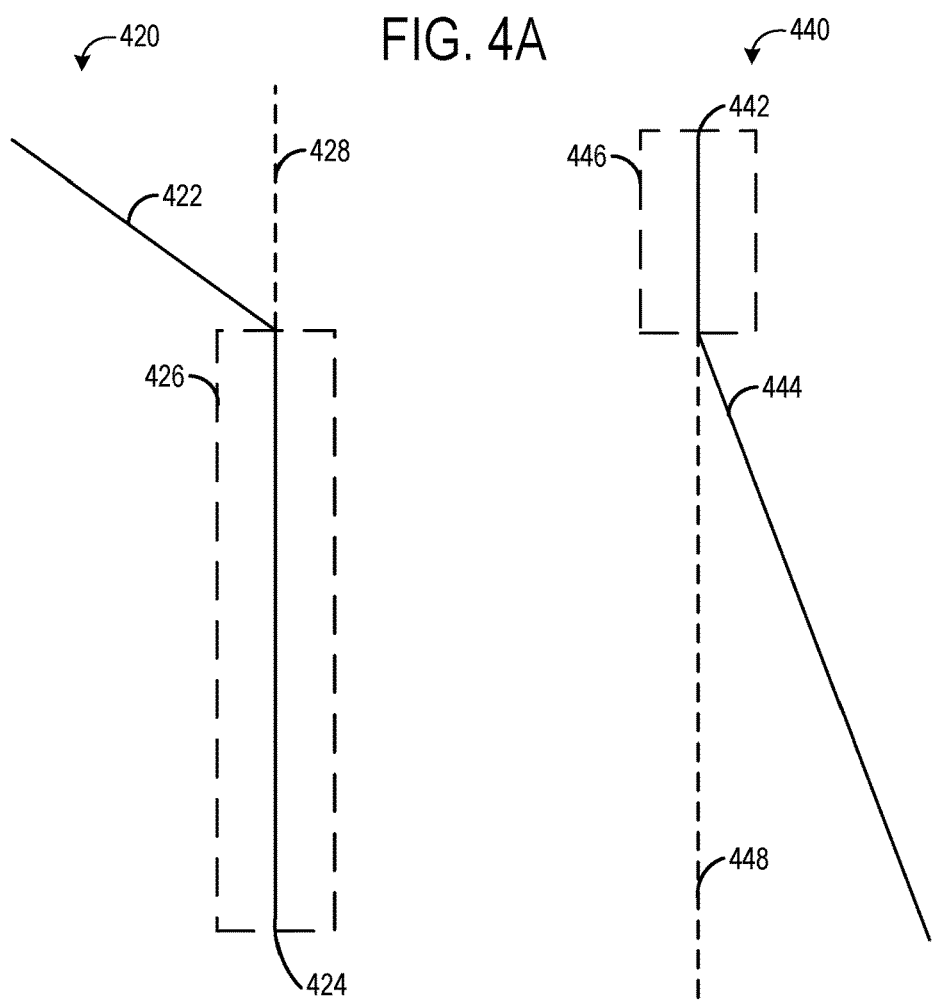
FIG. 4B
FIG. 4C ized uniquely by the claims
SYSTEM AND METHODS FOR BEAMFORMING SOUND SPEED SELECTION

TECHNICAL FIELD

Embodiments of the subject matter disclosed herein relate to ultrasound imaging, and more particularly, to improving image quality for ultrasound imaging.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be saved for later analysis by a clinician to aid in diagnosis and/or displayed on a display device in real time or near real time.

SUMMARY

In one embodiment, a method for an ultrasound system including a plurality of ultrasound transducers each coupled to a respective receive channel includes time-delaying a set of ultrasound receive channel signals to form a plurality of time-delayed sets of ultrasound receive channel signals, each time-delayed set of ultrasound receive channel signals time-delayed based on a different beamforming sound speed, calculating a beamforming quality metric for each receive channel and for each time-delayed set of ultrasound receive channel signals, and generating an ultrasound image from ultrasound receive channel signals selected from the plurality of time-delayed sets of ultrasound receive channel signals based on each beamforming quality metric.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which:

FIGS. 4A-4C show ultrasound waves traveling through different mediums with an assumed speed of sound compared to an actual speed of sound as well as aligned channel data after applying time delays;

DETAILED DESCRIPTION

Figure 1:
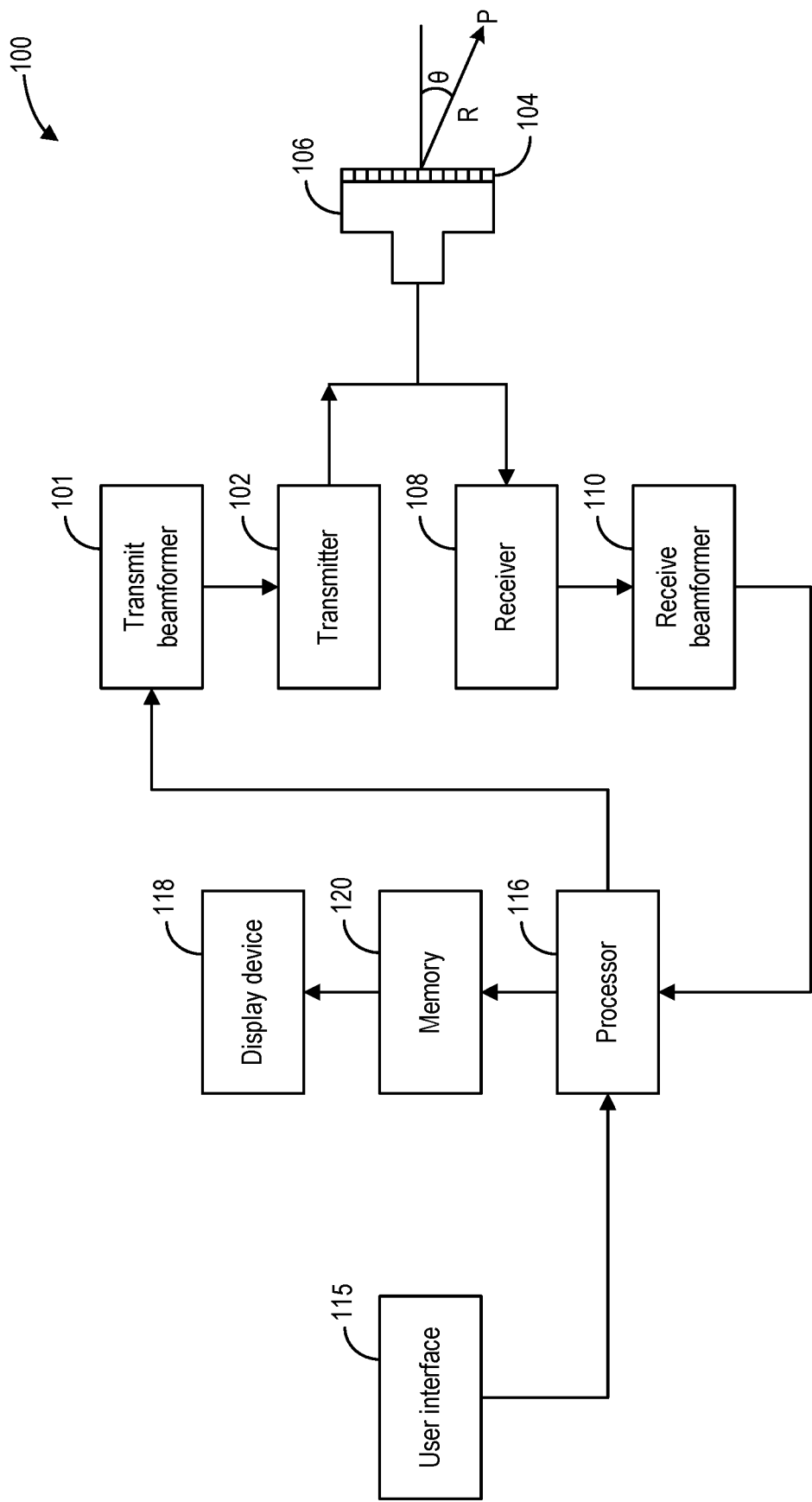
FIG. 1 shows a block diagram of an exemplary embodiment of an ultrasound system.

Medical ultrasound imaging typically includes the placement of an ultrasound probe including one or more transducer elements onto an imaging subject, such as a patient, at the location of a target anatomical feature (e.g., abdomen, chest, etc.). Images are acquired by the ultrasound probe and are displayed on a display device in real time or near real time (e.g., the images are displayed once the images are generated and without intentional delay). During a procedure when the ultrasound probe acquires an image, transmit beamforming and receive beamforming may be used. Time delays may be implemented during transmit beamforming and receive beamforming to alter an angle and focus range of beamforming when acquiring the ultrasound image. Beamforming time delays may be based on an assumed speed that ultrasound waves travel through an imaging medium (e.g., tissue). Such an assumed speed may typically be a default speed set by the system. Different imaging mediums (e.g., fatty tissue, liver tissue) exhibit different sound propagation speeds, meaning a speed at which ultrasound travels through a first medium may be different from a speed at which ultrasound travels through a second medium. As a result, a predetermined or default assumed speed set by the system may result in a loss of image resolution depending on the imaging medium or variance of imaging mediums covered during an ultrasound scan. Conventional ultrasound systems may allow an ultrasound operator to manually adjust the assumed sound speed used in calculating beamforming time delays, but various factors may inhibit proper selection of the sound speed (e.g., user inexperience, time constraints) which may result in ultrasound images exhibiting lower resolutions. In addition, a single assumed sound speed may not be optimal when the sound speed varies within the medium. Moreover, manufacturers of ultrasound systems find that a majority of operators dislike having to make manual adjustments on an ultrasound system to optimize an ultrasound image quality.

Thus, according to embodiments disclosed herein, optimal receive beamforming time delays may be automatically applied for each receive channel coupled to a respective transducer element in an ultrasound probe, for each depth and at upon each transmit event, such that a generated ultrasound image may exhibit an improvement to image resolution. Ultrasound data received by the transducers of the ultrasound probe, prior to processing into an image (referred to herein as channel data), may be time-delayed a plurality of times based on different beamforming sound speeds and analyzed to identify which beamforming sound speed and corresponding time delay to apply to each receive channel to generate the image. To identify the time delay to apply to each receive channel, a beamforming quality metric may be determined for each receive channel and each different time delay, where the beamforming quality metric may be based on a coherence factor that reflects a level of similarity among a subset of receive channel signals centered over the receive channel under calculation. In this way, an ultrasound image generated from automatically selected ultrasound imaging parameters may exhibit higher image resolutions without operator intervention.

For example, an original undelayed set of channel signals may be acquired and stored in memory. Assuming a set of possible speed of sounds values includes 20 speed of sound values, then 20 time-delayed versions of the original undelayed channel signals are created, where each version is delayed with one of the 20 Speed of Sound (SOS) values. Every sample of the delayed channel data signals will be alternatively called pixel in the following explanation. Then for every transmit, in every delayed channel signal, the following may be performed: for every depth, a coherence metric for every channel is calculated. The coherence metric is calculated using channels adjacent to that channel under calculation. For every depth, and for every channel, the pixel (e.g., time-delayed channel signal sample) from the SOS delayed channel signal set that has the highest coherence score is selected. In some examples, instead of calculating the coherence metric for every depth, the coherence metric can be calculated for a block of depths at once to improve speed. Further, instead of taking the pixel with highest coherence metric out of the different SOS delayed channel signals, a weighted average of the pixels/time delayed channel signals may be calculated (e.g., for every set of SOS delayed channel signals for a channel and depth, select the corresponding pixel, and instead of taking the pixel with the highest coherence metric, take a weighted average of all the possible pixels). Further still, instead of selecting individual pixels from SOS delayed channel signals, for every transmit and depth, contiguous islands of channels with coherence metrics above a certain threshold in every SOS dataset can be identified. Then if a channel belongs to several islands, the island with bigger size would be the one to contain this channel in the final combination of the islands from the different speed of sound datasets. That will be implicitly choosing the largest coherent aperture from every delayed dataset. As an alternative, the quality metric of every pixel may be proportional to its coherency with its neighboring channels and the size of the coherent aperture it belongs to in that SOS dataset. Then, the pixel with highest quality score from the SOS dataset is selected.

Figure 2:
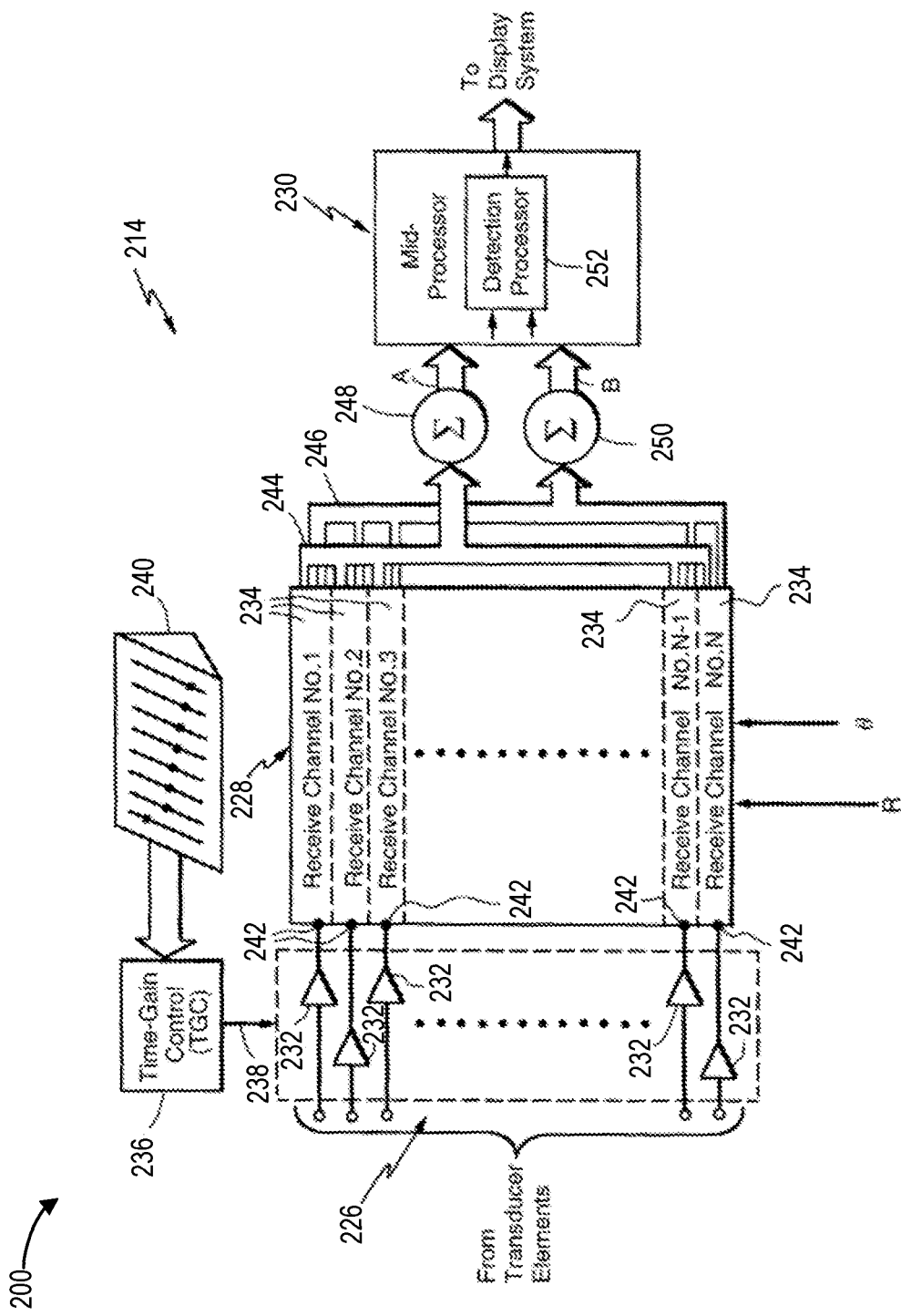
FIG. 2 is a block diagram showing a receiver which forms part of the system of FIG. 1.
Figure 3:
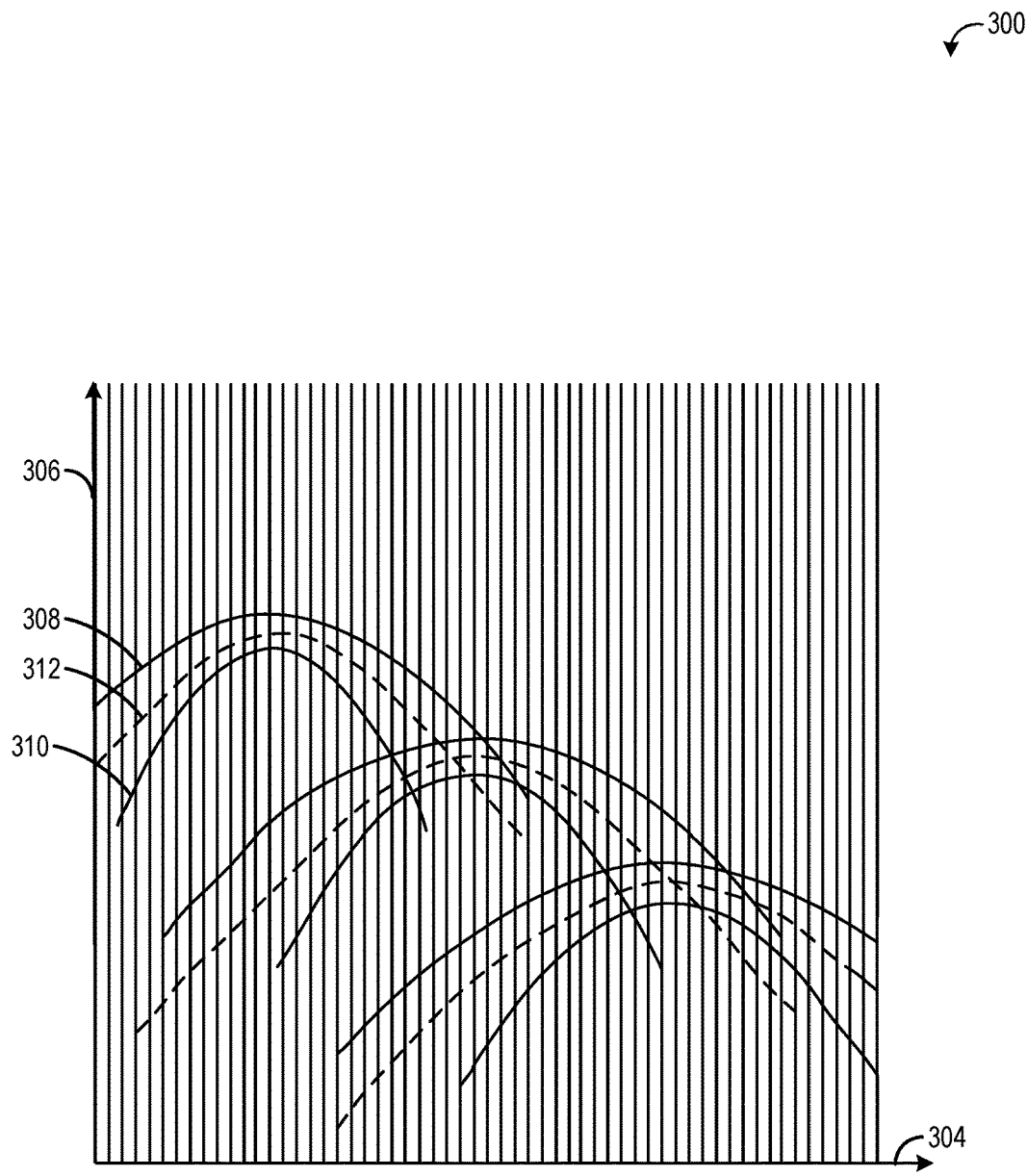
FIG. 3 is a diagram illustrating hyperbolic signatures of the time delays of received radio frequency signals.
Figure 6:
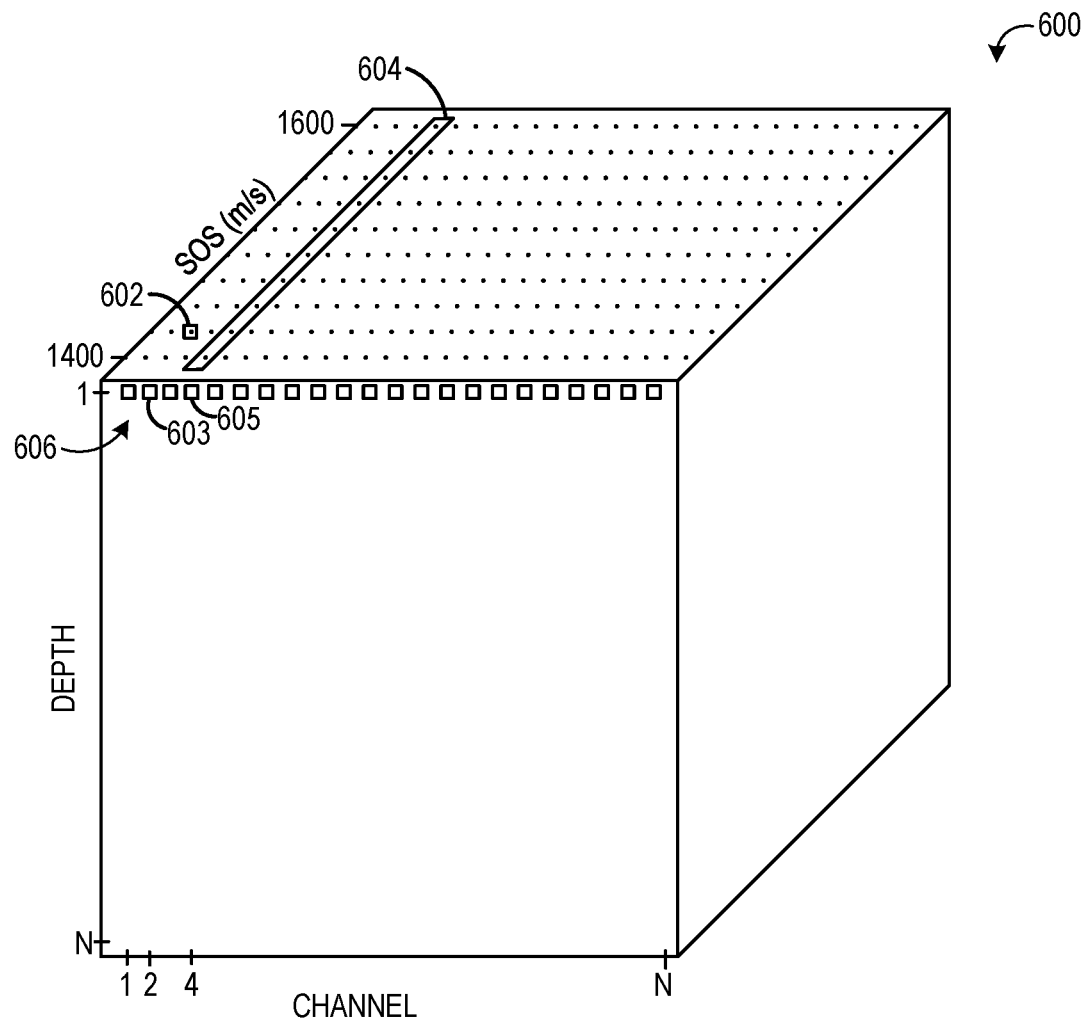
FIGS. 6 and 7 are diagrams schematically illustrating beamforming quality metrics calculated on receive channel signals time delayed based on a plurality of sound speeds and for a plurality of depths.
Figure 7:
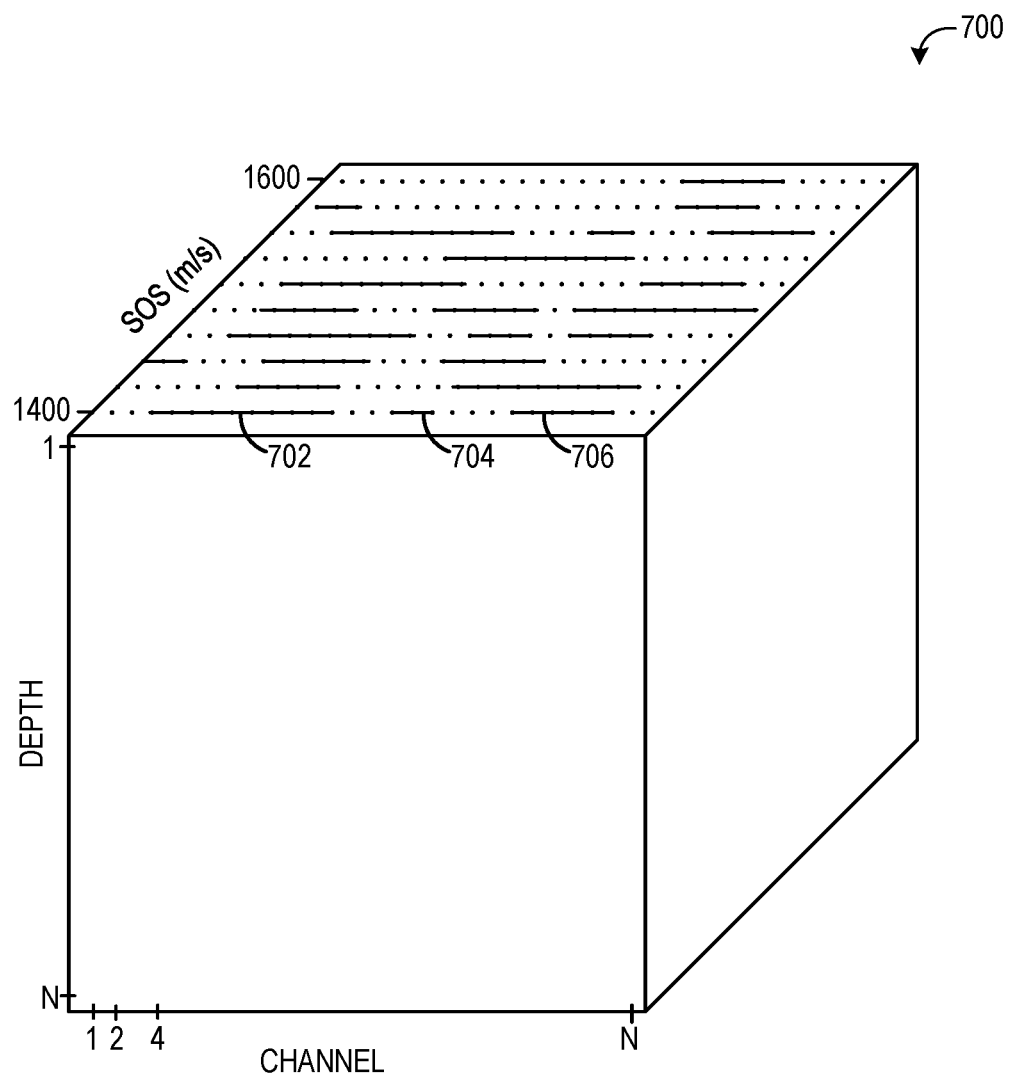

An example ultrasound system including an ultrasound probe, a display device, and an imaging processing system are shown in FIG. 1. Via the ultrasound probe, ultrasound images may be acquired and displayed on the display device. A receiver of the system of FIG. 1 with multiple receive channels for receive beamforming is shown in FIG. 2. A graph illustrating hyperbolic signatures of the delay of received radio frequency signals is shown in FIG. 3. An example schematic illustration of ultrasound waves reflected off a point and traveling through different mediums during ultrasound imaging is shown in FIG. 4A. A first alignment of channel data based on a first sound speed is shown in FIG. 4B. A second alignment of channel data based on a second sound speed is shown in FIG. 4C. Optimal beamforming sound speeds may be determined for each channel and applied to time delay channel signals to generate an ultrasound image according to the method of FIG. 5. Graphs illustrating beamforming quality metrics for each receive channel calculated at a plurality of different sound speeds and for each of a plurality of depths for a receive beam are shown in FIGS. 6 and 7.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic wave. In this way, transducer elements 104 may convert electronic transmit signals into acoustic transmit beams.

After the elements 104 of the probe 106 emit pulsed ultrasonic signals into a body (of a patient), the pulsed ultrasonic signals reflect from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data.

The echo signals produced by transmit operation reflect from structures located at successive ranges along the transmitted ultrasonic beam. The echo signals are sensed separately by each transducer element and a sample of the echo signal magnitude at a particular point in time represents the amount of reflection occurring at a specific range (also referred to as depth). Due to the differences in the propagation paths between a reflecting point P and each element, however, these echo signals are not detected simultaneously. Receiver 108 amplifies the separate echo signals, imparts a calculated receive time delay to each amplified signal, and sums the time-delayed, amplified signals to provide a single echo signal which approximately indicates the total ultrasonic energy reflected from point P located at range R along the ultrasonic beam oriented at angle θ.

The time delay of each receive channel continuously changes during reception of the echo to provide dynamic focusing of the received beam at the range R from which the echo signal is assumed to emanate based on an assumed sound speed for the medium.

Under direction of processor 116, the receiver 108 provides time delays during the scan such that steering of receiver 108 tracks the direction θ of the beam steered by the transmitter and samples the echo signals at a succession of ranges R so as to provide the proper time delays and phase shifts to dynamically focus at points P along the beam. Thus, each emission of an ultrasonic pulse waveform results in acquisition of a series of data points which represent the amount of reflected sound from a corresponding series of points P located along the ultrasonic beam.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the real RF data and generates complex data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Turning now to FIG. 2, it shows an embodiment 200 of a receiver 214 comprising three sections, including a time-gain control section 226, a receive beamforming section 228, and a mid-processor 230. In one example, receiver 214 may be a non-limiting example of receiver 108 of FIG. 1. The time-gain control (TGC) section 226 includes a respective amplifier 232 for each of the receive channels 234, and a time-gain control circuit 236 is provided for controlling gain of amplifiers 232. The input of each amplifier 232 is coupled to a respective one of transducer elements 104 to amplify an echo signal which it receives. The amount of amplification provided by amplifiers 232 is controlled through a control line 238 driven by TGC circuit 236, the latter being set by hand operation of potentiometers 240.

The receive beamforming section 228 of receiver 214 includes a plurality of receive channels 234, each receive channel 234 receiving the analog echo signal from a respective amplifier 232 at a respective input 242. The analog signals are digitized and produced as a stream of signed digitized samples. These samples are respectively delayed in the receive channels such that when they are summed with samples from the other receive channels, the amplitude of the summed signals of the selected channels is a measure of the strength of the echo signal reflected from a point P located at range R on the steered beam θ.

To properly sum electrical signals produced by the echoes impinging on each transducer element 104, time delays are introduced into each separate channel 234 of receiver 214. The time delay that is added to each receive channel may be based on an assumed speed of sound through the imaged tissue. In one example, the imaged tissue may include more fat than muscle in certain regions, affecting the time delay that may be applied when receive beamforming over that region as a result of a difference in propagation speed when ultrasound passes through fat and when ultrasound passes through muscle. Each receive channel 234 supplies, in addition to the delayed signed samples, the amplitude, or absolute value, of the delayed signed samples. The delayed signed samples are provided to a coherent summation bus 244, while the amplitudes of the delayed, signed samples are provided to an incoherent summation bus 246. Coherent summation bus 244 sums the delayed signed samples from any number of contiguous receive channels using pipeline summers 248 to produce a coherent sum (e.g., coherent sum A in FIG. 2). Incoherent summation bus 246 sums the amplitudes of the delayed signed samples from any number of contiguous receive channels using pipeline summers 250 to produce an incoherent sum (e.g., incoherent sum B in FIG. 2).

Receiver mid-processor section 230 receives the coherently summed beam samples from pipeline summers 248 and receives the incoherently summed beam samples from pipeline summers 250. Mid-processor section 230 comprises a detection processor 252.

Detection processor 252 calculates and applies a coherence factor in accordance with the present disclosure. The coherence factor may be calculated for each data sample/channel signal and may be defined (at least in one example) to be the ratio of two quantities: the amplitude of the sum of the receive signals and the sum of the amplitudes of the receive signals. The ratio is calculated in detection processor 252 by calculating the absolute value of the coherent sum from pipeline summers 248 and then calculating the ratio of the absolute value of the coherent sum from pipeline summers 248 to the incoherent sum from pipeline summers 250. If the incoherent sum is zero, the ratio may be set to zero. In one example, the ratio may be calculated by dividing the absolute value of the coherent sum by the sum of the incoherent sum and a small positive value, which may avoid dividing by zero when the incoherent sum is zero. In one example, detection processor 252 is a non-limiting example of processor 116 of FIG. 1. In another example, detection processor 252 is separate from, but operably coupled to, processor 116 of FIG. 1.

For the case of a radio frequency (RF) beamformer, the signal from each channel is a real, signed quantity and the coherent sum is the sum of the signals. The incoherent sum is the sum of the absolute value of each signal (e.g., a sum of non-negative numbers). For the case of a baseband beamformer, the real signal from each channel is demodulated to form a complex quantity, so that the coherent sum is also a complex quantity. The absolute value of the coherent sum is a non-negative real quantity. The incoherent sum is the sum of the absolute values of the channel signal; it is a non-negative real quantity. In both cases, the ratio of the absolute value of the coherent sum to the incoherent sum is a non-negative real quantity.

During an ultrasound scan, a transmitter may drive a probe such that ultrasonic energy produced may be directed in a beam. To accomplish this, the transmitter may impart a time delay to pulsed waveforms that may be applied to successive transducer elements in the probe. By adjusting time delays in a conventional manner, the beam of ultrasonic energy may be directed away from an axis parallel to the probe by some angle, focusing the beam at a fixed range. By successively changing the time delays, an ultrasound scan may be performed as a result of the angle the beam may be directed at progressively changing.

A receive ultrasound beamformer may be used as part of an ultrasound imaging system. The ultrasound imaging system may use a transmit event from a transmit beamformer and a receive event from the receive beamformer to generate one line of an ultrasound image. The transmit beamformer may focus at one location of a scanning region, and the receive beamformer may focus at the same location. During receive beamforming, time delays may be associated with a propagation of ultrasound waves in relation to an angle and a speed at which an ultrasound wave is received by the receive beamformer.

Due to differing sound propagation speeds of anatomical mediums in an anatomical region, a speed at which an ultrasound wave propagates during an ultrasound scan may vary. A default propagation speed may be considered for the ultrasound scan depending on the anatomical region the probe may be transmitting over, which may be prone to error, resulting in lower image resolutions. Errors from using a default propagation speed during an ultrasound scan may occur in scanning regions that include muscle, fat, and bone, as a result of ultrasound waves propagating at different speeds through all mediums. When a receive beamformer operates with a default propagation speed that differs from an actual propagation speed, data received may be calculated erroneously, resulting in inaccurate imaging during a generation of an ultrasound image. In one example, an ultrasound scan may occur over a region including muscle and fat, which have differences in their associated sound propagation speeds, and a generated ultrasound image from the ultrasound scan may include regions of low resolution as a result of suboptimal beamforming sound speeds for the region. Automatically selecting an optimal beamforming sound speed for each channel may result in optimizing metrics of ultrasound image generation.

Turning now to FIG. 3, it shows an example of a graph 300 depicting hyperbolic signatures in radio frequency signals. The hyperbolic signatures represent the relative difference in time that each RF signal travels along each channel, for three echoes reflected from three different points/scatterers during an ultrasound scan. The echoes, when detected by ultrasound transducers, may be converted into RF signals to be received by receive channels during receive beamforming.

A first axis 304 represents receive channels in an ultrasound imaging system, where each perpendicular line extending from first axis 304 represents an individual channel. A second axis 306 represents time, such that values of time closer to first axis 304 may be smaller than values of time further from first axis 304.

The dashed line hyperbolas, such as hyperbola 312, are generated when the speed of sound of the scatterer and/or medium through which the echoes travel is a nominal speed of sound, such as 1540 m/s. The outer solid line hyperbolas, such as hyperbola 308, are generated when the speed of sound of the scatterer and/or medium is greater than the nominal speed of sound. The inner solid line hyperbolas, such as hyperbola 310, are generated when the speed of sound of the scatterer and/or medium is less than the nominal speed of sound.

As appreciated by FIG. 3, the shape of the hyperbola changes based on the speed of sound. For example, hyperbola 308 is flatter than hyperbola 310 and hyperbola 312. Further, different mediums may result in different shaped hyperbolas. Thus, when time delays are added to each RF signal prior to summing the RF signals during image generation, the time delays are selected based on the speed of sound of the medium. In general, ultrasound images may be generated by applying an assumed speed of sound (e.g., 1540 m/s). However, if the speed of sound of the medium is different than the assumed speed of sound, the time delays that are added may not match the shape of the hyperbola, leading to image quality issues, as explained above.

Turning now to FIG. 4A, it shows an example schematic depiction 400 of a plurality of portions of an ultrasound beam 401 returning from a point 402 to one or more transducers of an ultrasound probe. The plurality of portions of the ultrasound beam 401 may propagate through multiple anatomical mediums when traveling from point 402 back to the transducers.

As explained previously, optimal ultrasound image generation may include accurately applying time delays based on an assumed speed of sound for each portion of an ultrasound beam. A first curve 408 may represent an assumed time of arrival for the ultrasound beam at the transducers for the portions of the ultrasound beam based on the assumed speed of sound that each portion of the ultrasound beam may be traveling at through the anatomical scanning region. However, as appreciated by FIG. 4A, not all portions of an ultrasound beam may travel through the same medium and thus in actuality, one or more portions of a beam may arrive at the ultrasound transducers at a time different than that expected according to the assumed speed of sound.

Thus, as shown, a first portion 404 of the ultrasound beam may propagate from point 402 back to the transducers, accurately matching the time of arrival predicted by first curve 408. A second portion 405 of the ultrasound beam may propagate from point 402 back to the transducers, but because second portion 405 of the ultrasound beam travels through a medium 406, second portion 405 of the ultrasound beam may not have a time of arrival that accurately matches first curve 408 as a result of propagating through a different medium than first portion 404 of the ultrasound beam. Portions of the ultrasound beam traveling through medium 406 may have a time of arrival represented by second curve 410.

Applying time delays to the plurality of portions of the ultrasound beam based on the assumed speed of sound represented by first curve 408 may lead to inaccurate time delays applied to portions of the ultrasound beam propagating through medium 406. Applying inaccurate time delays may lead to lower image quality (e.g., image resolution) when generating ultrasound images based on one assumed speed of sound.

FIG. 4B shows an example schematic illustration of a first alignment 420 of channel signals based on applied time delays derived from a first speed of sound. When time delays are applied based on an assumed speed of sound that is accurate for all portions of an ultrasound beam propagating from and to a transducer, all channel signals may align along a vertical axis 428. In one example, first alignment 420 may represent an alignment of ultrasound channel signals when a first set of time delays are applied to the channel signals obtained when the ultrasound beam from FIG. 4A is received by the ultrasound transducers based on a first assumed speed of sound.

A first section 422 of first alignment 420 may include channel signals from the channels coupled to ultrasound transducers that receive the portions of the ultrasound beam that traveled through medium 406. First section 422 may represent receive channels where time delays applied based on the first assumed speed of sound may be inaccurate compared to an actual speed of sound for the portions of the ultrasound beam during propagation, and thus the channel signals in first section 422 are not aligned along vertical axis 428. A second section 424, bounded by a first bounding box 426, may include the channel signals from the channels where time delays applied based on the first assumed speed of sound may be accurate compared to an actual speed of sound for the portions of the ultrasound beam during propagation (e.g., the transducers that receive the portions of the ultrasound beam that did not travel through the medium 406). As visually indicated by FIG. 4B, when the channel signals are summed during image generation, the channel signals parallel with vertical axis 428 may exhibit a high level of coherence relative to each other, explained in detail with respect to FIG. 2, and the channel data not parallel with vertical axis 428 may exhibit lower coherence relative to the channel data in the second section 424.

FIG. 4C shows an example schematic illustration of a second alignment 440 of channel signals based on applied time delays derived from a second speed of sound. In one example, second alignment 440 may represent an alignment of ultrasound channel signals when a second set of time delays are applied to each channel signal obtained when the ultrasound beam from FIG. 4A is received by the ultrasound transducers based on a second assumed speed of sound.

A third section 442 of second alignment 440, bounded by a second bounding box 446, may include channel signals from the channels coupled to ultrasound transducers that receive the portions of the ultrasound beam that traveled through medium 406. Third section 442 may represent ultrasound channels where time delays applied based on the second assumed speed of sound may be accurate compared to an actual speed of sound for the portions of the ultrasound beam during propagation, and thus the channel signals in third section 442 are aligned along vertical axis 448. A fourth section 444 may include the channel signals from the channels where time delays applied based on the second assumed speed of sound may not be accurate compared to an actual speed of sound for the portions of the ultrasound beam during propagation (e.g., the transducers that receive the portions of the ultrasound beam that did not travel through the medium 406). As visually indicated by FIG. 4C, when the channel signals are summed during image generation, the channel signals parallel with vertical axis 448 may exhibit a high level of coherence relative to each other, explained in detail with respect to FIG. 2, and the channel signals not parallel with vertical axis 448 may exhibit lower coherence relative to the channel signals in the third section 442.

Thus, as shown in FIG. 4A, even from a single point source, ultrasound echoes may propagate at different speeds, so applying a single beamforming sound speed to time-delay each channel signal may result in lower image quality. FIGS. 4B-4C represent two time-delays of channel signals from the same set of channel signals using two different beamforming sound speeds. As demonstrated by FIGS. 4B and 4C, using the same beamforming sound speed to time delay receive channel signals across all channels may result in some channel signals being misaligned, even while other channel signals are more accurately aligned. According to embodiments disclosed herein, a channel-based method of choosing optimal beamforming sound speeds and hence time delays for each receive channel independently may lead to generating an ultrasound image with higher image metrics (e.g., image resolution) than generating an ultrasound image using channel signals where only one beamforming sound speed is chosen to time delay all channel signals. In one example, if the first sound speed from FIG. 4B is applied to the receive channels in the second section 424 and the second sound speed from FIG. 4C is applied to the receive channels in the third section 442, all receive channel data may align. As will be explained in more detail below, an optimal beamforming sound speed may be determined for each receive channel. Embodiments are disclosed for selecting an optimal or target beamforming sound speed on a channel by channel basis.

Figure 5:
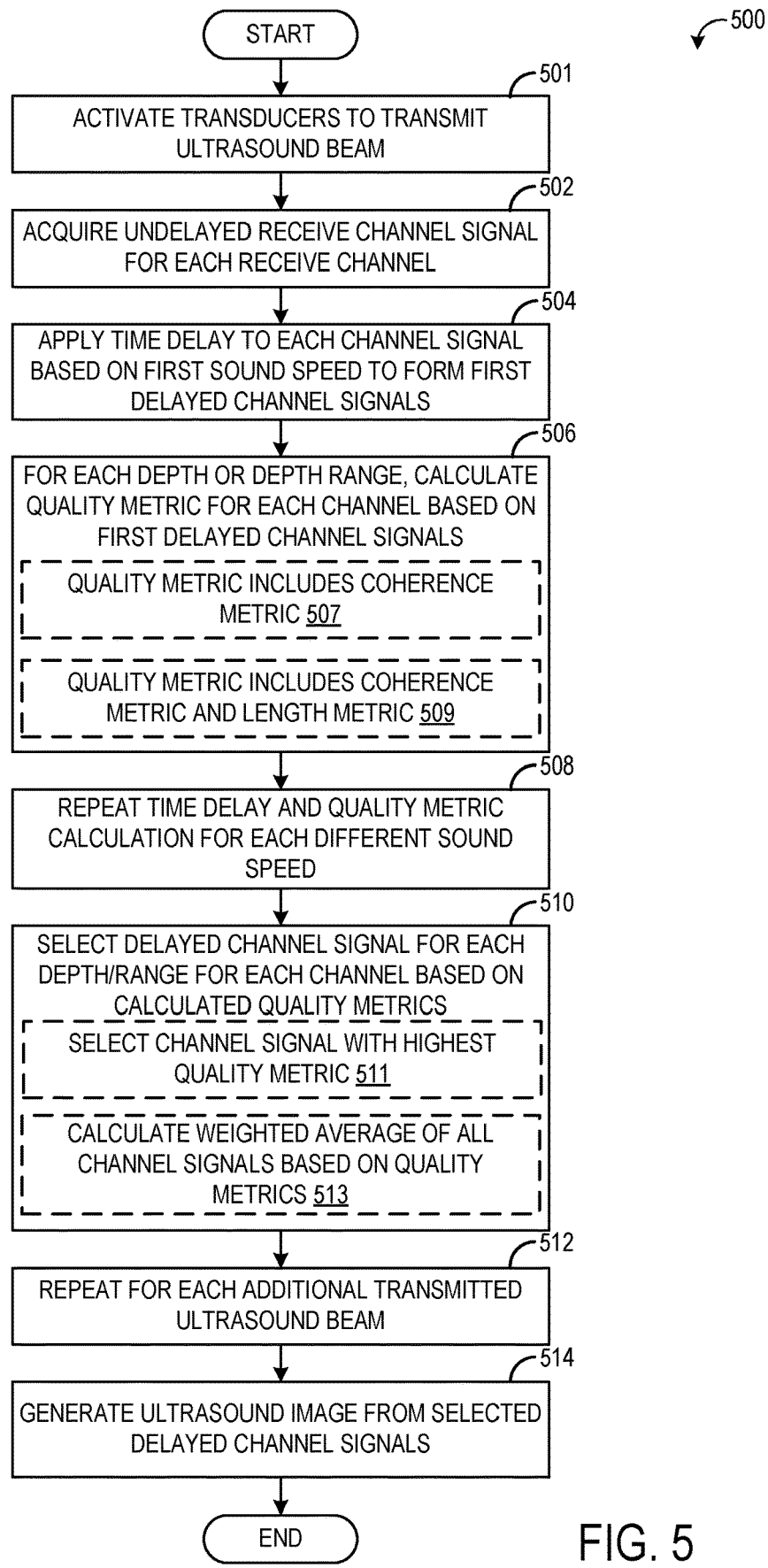
FIG. 5 is a flow chart illustrating an example method for generating an ultrasound image from receive channel signals selected based on beamforming quality metrics calculated for each channel and for each of a plurality of different time delays during an ultrasound scan.

FIG. 5 shows a flow chart illustrating an example method 500 for generating an ultrasound image using time delays selected for each receive channel independently based on beamforming quality metrics. Method 500 is described with regard to the systems and components of FIG. 1-2, though it should be appreciated that the method 500 may be implemented with other systems and components without departing from the scope of the present disclosure. Method 500 may be carried out according to instructions stored in non-transitory memory of a computing device, such as processor 116. In some examples, method 500 may be carried out each time ultrasound data is acquired by the ultrasound probe and an image is formed from the ultrasound data, such that the frequency that method 500 is executed matches the frame rate of the ultrasound imaging. In other examples, method 500 may be carried out at a predetermined frequency during ultrasound imaging that is less than the frame rate (e.g., once per second) and/or in response to a determination that the ultrasound probe has been moved or that the anatomy being imaged has changed.

At 501, method 500 includes activating a plurality of ultrasound transducers of an ultrasound probe to transmit an ultrasound beam toward a subject being imaged. The transmitted ultrasound beam may be focused at a specific focal depth and beam angle. At 502, method 500 includes acquiring an undelayed channel signal from each transducer in the ultrasound probe, such as the receive channels 234 as illustrated and described with respect to FIG. 2. As explained above with respect to FIGS. 1-2, the channel signals include echoes detected by the ultrasound transducer elements, which are received following the transmitted beam.

At 504, method 500 includes applying a respective time delay to each channel signal based on a first sound speed to form a first delayed channel signal for each channel. The first sound speed may be a first sound speed of a set of possible sound speeds. The set of possible sound speeds may be predetermined or set by a user. In one example, the set of possible sound speeds may include 5, 10, 20, or more sound speeds within a range of reasonable sound speeds based on the imaging task (e.g., imaging human anatomy may result in a range of 1400 m/s to 1600 m/s). As explained previously, the reflected echoes from a desired source point to the transducer elements. The arrival time of the echo (e.g., receive beam) at the transducer elements may be a function of the distance from the source point to the transducer element and the sound speed of the medium through which the ultrasound waves travel (e.g., distance (source, transducer_element)/medium_sound_speed in the case in which the sound speed in the medium is a constant). When the sound speed in the medium is not constant, the arrival time at the transducer elements is an integral over the incremental propagation times along the assumed propagation path, where the incremental propagation times are the incremental distances along the path divided by the sound speeds at each incremental distance. Thus, beamforming is performed to remove the assumed differences in arrival time at the transducer elements, typically using a single assumed sound speed for the medium, then the time-delayed signals are summed to form the image (explained below). If the assumed beamforming sound speed is different from the true sound speed in the medium, the beamforming will be sub-optimal and less than optimal image resolution and contrast may result. Thus, as explained herein, beamforming may be performed on the same channel signals with different sound speeds to identify the target or optimal sound speed for each channel for forming the image, based on a beamforming quality metric calculated for each receive channel at each different sound speed.

At 506, method 500 includes calculating a beamforming quality metric for each receive channel from the first delayed channel signals. The beamforming quality metric may be calculated for each receive channel at each depth of the receive beam/imaged tissue. In other examples, the depths may be combined into a plurality of ranges of depths and a beamforming quality metric may be calculated for each range of depths. For example, a beamforming quality metric may be calculated for a first depth, and this beamforming quality metric may be applied to one or more depths above and/or below the first depth (e.g., 2-3 depths above and 2-3 depths below the first depth), which may reduce the number of beamforming quality metrics that are calculated and hence may increase the speed at which the time-delayed channel signals are selected (e.g., as explained below). The depth ranges may be overlapping (as explained above) or non-overlapping. Each beamforming quality metric may include a coherence metric, as indicated at 507, that represents a level of similarity among a subset of delayed channel signals, which is correlated with image resolution and contrast but does not require an image to be formed. In one example, the coherence metric may be the coherence factor described above with respect to FIG. 2. However, other methods for determining the coherence metric are possible without departing from the scope of this disclosure, such as a ratio of the squared amplitude of the channel signals, a similarity of the phases of complex channel signals, or a similarity of the signs of real channel signals.

For the purposes of calculating the coherence metrics, the receive channels may be partitioned into subsets of channels by applying a moving window across the receive channels at each depth or depth range, with the widow positioned over (e.g., centered over) each receive channel in succession to calculate the coherence metric for that receive channel at that depth based on the delayed channel signals for that receive channel and one or more adjacent receive channels, at that depth or depth range. For example, at a first depth (or depth range), a first coherence metric for the first receive channel may be calculated from the time-delayed channel signal at the first depth received over the first receive channel and the time-delayed channel signal received over the second receive channel (adjacent to the first receive channel) at the first depth. A second coherence metric for the second receive channel may be calculated from the time-delayed channel signal received over the first receive channel, the time-delayed channel signal received over the second receive channel, and the time-delayed channel signal received over the third receive channel (adjacent to the second receive channel), all at the first depth. The moving window may be sized to calculate each coherence metric from three adjacent/contiguous receive channels (other than the first and last channels), or another suitable number of adjacent/contiguous receive channels (e.g., 2, 5, 7, etc.). As explained previously, the coherence metric may be a normalized value ranging from 0 to 1, inclusively, where 1 means high confidence that the magnitude of the beamsum from those receive channels at that depth represents the scattering from the intended focus direction and values closer to 0 may indicate that spurious and/or off-axis scattering may be present in the receive channel signals.

In some examples, each beamforming quality metric may include a coherence metric and a length metric, as indicated at 509. The coherence metric may be calculated for each receive channel at each depth, as explained above. To calculate the length metric, the coherence metrics calculated for all receive channels at a given depth may be filtered to identify the coherence metrics above a threshold value (e.g., above 0.5, or the top 10-50% of the coherence metrics). Contiguous receive channels having a coherence metric above the threshold value may be identified as high coherence islands and each receive channel in a high coherence island may be assigned a length metric value that is directly proportional to the number of receive channels in that high coherence island. For example, each receive channel in a first high coherence island having 10 contiguous receive channels may be assigned a length metric of 0.1 while each receive channel in a second high coherence island having 20 contiguous receive channels may be assigned a length metric of 0.2. In one example, each receive channel in a high coherence island may be assigned a beamforming quality metric that includes the coherence metric for that receive channel and the length metric for each receive channel in that high coherence island, such that each receive channel in the high coherence island has a beamforming quality metric that is calculated independently. In another example, the coherence metrics and length metric for all receive channels in a high coherence island may be averaged and the averaged value may be assigned as the beamforming quality metric for each receive channel in that high coherence island, such that each receive channel in the high coherence island has the same beamforming quality metric. If a receive channel is not included in any high coherence island, that receive channel may be assigned a beamforming quality metric that is only based on that receive channel's coherence metric.

At 508, method 500 includes repeating 502-506 for each different sound speed of the set of possible sound speeds. For example, if the set of possible sound speeds includes 20 sound speeds, the original (e.g., undelayed) set of receive channel signals may be time-delayed for each additional sound speed, so that 20 time-delayed sets of receive channel signals are generated, with one set generated for each different sound speed. For each time-delayed set of receive channel signals, a beamforming quality metric is calculated for each receive channel at each depth (or depth range). In this way, a beamforming quality metric may be calculated for each receive channel, at each depth, and for each sound speed of the set of possible sound speeds.

At 510, method 500 includes selecting a time-delayed receive channel signal for each receive channel and at each depth or depth range based on the calculated beamforming quality metrics for the receive channels at the depth/depth range. In a first example, selecting a time-delayed receive channel signal for each receive channel and at each depth may include selecting the time-delayed receive channel signal with the highest beamforming quality metric, as indicated at 511. For example, when 20 different time-delayed sets of receive channel signals are generated, 20 different beamforming quality metrics may be calculated for a given receive channel at a given depth, each corresponding to a different time-delayed receive channel signal (where each different time-delayed receive channel signal is generated from the same, undelayed receive channel signal received over that receive channel and time-delayed based on the 20 different sound speeds). The highest beamforming quality metric of those 20 beamforming quality metrics may be identified, and the time-delayed channel signal that resulted in that highest beamforming quality metric may be chosen as the selected time-delayed channel signal for that receive channel and depth. Thus, for each receive channel and each depth, the time-delayed channel signal resulting in the highest beamforming quality metric (relative to the other time-delayed channel signals for that receive channel and depth) may be selected.

In another example, selecting a time-delayed receive channel signal for each receive channel and at each depth may include calculating a weighted average of all time-delayed channel signals for that receive channel and that depth based on the beamforming quality metrics for the time-delayed channel signals, and setting the selected time-delayed channel signal as the weighted average signal. Calculating the weighted average may include applying a weight to each time-delayed channel signal that is directly proportional to the beamforming quality metric calculated for that time-delayed channel signal. For example, as explained above, for a given receive channel and depth, 20 time-delayed receive channel signals may be formed, where each time-delayed receive channel signal is generated from the same, undelayed receive channel signal received over that receive channel and time-delayed based on the 20 different sound speeds. A beamforming quality metric is calculated for each of the 20 time-delayed receive channel signals. The 20 time-delayed receive channel signals may be averaged with a weight applied to each time-delayed receive channel signal that is proportional (e.g., linearly or non-linearly) to the beamforming quality metric calculated for that time-delayed receive channel signal.

At 512, the process described above (e.g., obtaining an undelayed set of receive channel signals at 502; time delaying each receive channel signal multiple times, each using a different beamforming sound speed at 504 and 508; calculating a beamforming quality metric for each channel and depth at 506 and 508; and selecting a time-delayed channel signal for each channel and depth at 510) is repeated for each additional transmitted ultrasound beam. Thus, for each receive beam (received after a transmit event), a time-delayed channel signal is selected for each depth and each receive channel based upon the calculated beamforming quality metrics.

At 514, method 500 includes generating an ultrasound image from the selected time-delayed channel signals. For example, for each depth of each receive beam, the selected time-delayed receive channel signals are summed to form a beamsum signal, a logarithm of an absolute value of the beamsum signal is determined, a scan conversion to square pixels is performed, and the pixels are scaled to 8-bit grayscale values to form the image. Method 500 then returns.

FIG. 6 shows an example graph 600 illustrating a plurality of time-delayed channel signals plotted as a function of receive channel, depth, and beamforming sound speed. Graph 600 depicts time-delayed receive channel signals obtained for a single transmit event (e.g., one receive beam), as explained above with respect to FIG. 5.

Graph 600 depicts receive channels along the horizontal axis (x-axis), depth along the vertical axis (y-axis), and speed of sound (SOS) applied to time delay the receive channel signals along the transverse axis (z-axis). The receive channels increase in number from a first channel through a last channel (channel N). Depth increases from a top of the vertical axis down toward the horizontal axis, such that a smallest depth (e.g., the first depth) is closest to the ultrasound probe and a largest depth (depth N) is the furthest from the ultrasound probe. The SOS may include a plurality of SOSs selected from a range of possible SOSs, and increase in value from a first SOS (e.g., 1400 m/s) to a last SOS (e.g., 1600 m/s). The time-delayed receive channel signals are illustrated as the dots in graph 600. For clarity, only the time-delayed channel signals for the first depth are shown.

In the example shown, an ultrasound scan is performed such that echoes are received from a subject following transmission of ultrasound signals via an ultrasound probe. The echoes are received by the ultrasound transducers of the ultrasound probe and the output of each transducer is sent along the channels for processing, as described above. The channel signals are then sequentially processed with different time delays based on a plurality of different sound speeds (e.g., 10 or 20 speeds between 1400 m/s and 1600 m/s). As explained above with respect to FIG. 5, a beamforming quality metric is calculated for each time-delayed channel signal at each depth. In one example, the beamforming quality metrics may be calculated from a measure of the coherence of the receive signals, such as the coherence ratio, calculated in mid-processor 230 in FIG. 2 as a ratio of an amplitude of receive signals summed coherently and an amplitude of receive signals summed incoherently.

To form a scan line of an image, at each depth, selected time-delayed channel signals may be summed, thereby forming a beamsum for each depth. The beamsums are then converted to grayscale pixels as described above. The time-delayed channel signals are selected from among all the time-delayed channel signals (for that receive channel and depth) based on the beamforming quality metrics (calculated for that receive channel and depth). As explained above with respect to FIG. 5, one example for selecting the time-delayed channel signals includes selecting the time-delayed channel signal having the highest beamforming quality metric. For example, as shown in FIG. 6, for channel 2, 10 different beamforming quality metrics are calculated: one beamforming quality metric for each time-delayed channel signal, where each time-delayed channel signal is time delayed based on a different speed of sound. A time-delayed channel signal 602 (highlighted in FIG. 6 via a box for visual clarity) is selected, due to time-delayed channel signal 602 having a beamforming quality metric that is the highest beamforming quality metric of all the beamforming quality metrics calculated for channel 2 at the first depth. Thus, for the first depth, the channel signal received over channel 2 that was time-delayed by the second SOS is selected as the time-delayed channel signal 603 for channel 2 for the first depth.

Another example for selecting the time-delayed channel signals includes calculating a weighted average of all time-delayed channel signals for a receive channel and depth. For example, FIG. 6 illustrates this example of selecting the time-delayed channel signals for channel 4. All of the time-delayed channel signals for the first depth for channel 4 are indicated via box 604. These time-delayed channel signals for the first depth for channel 4 are averaged, with a respective weight applied to each time-delayed channel signal that is based on the beamforming quality metric calculated for that time-delayed channel signal. For example, if the beamforming quality metric calculated for the time-delayed channel signal time-delayed by the first SOS is higher than the beamforming quality metric calculated for the time-delayed channel signal time-delayed by the last SOS, a higher weight will be applied to the time-delayed channel signal time-delayed by the first SOS. Thus, for the first depth, the channel signals received over channel 4 that were time-delayed by all the SOSs are averaged with a weighted averaging scheme that applies weights in proportion to the corresponding beamforming quality metric, and the averaged signal is selected as the time-delayed channel signal 605 for channel 4 for the first depth. Once a time-delayed channel signal is selected for each receive channel, that plurality of time-delayed channel signals 606 for the first depth is summed and further processed to form a pixel of the final image. A similar process is performed at each depth, thereby forming a scan line of the final image. This whole process is repeated for each transmit/receive beam to form the final image.

FIG. 7 shows a graph 700 that is similar to graph 600, and thus illustrates a plurality of time-delayed channel signals plotted as a function of receive channel, depth, and beamforming sound speed, for a single transmit event (e.g., one receive beam). The time-delayed receive channel signals are illustrated as the dots in graph 700. For clarity, only the time-delayed channel signals for the first depth are shown.

FIG. 7 schematically illustrates a plurality of high coherence islands, where each receive channel has a coherence metric above a threshold for that depth and SOS (applied to time-delay the channel signals used to calculate the coherence metric). For example, for the first SOS (1400 m/s) and the first depth, a first high coherence island 702, a second high coherence island 704, and a third high coherence island 706 are present. Each receive channel in the first high coherence island 702 may be assigned a first length metric (in addition to the coherence metric calculated for each receive channel), each receive channel in the second high coherence island 704 may be assigned a second length metric, and each receive channel in the third high coherence island 706 may be assigned a third length metric, with the first length metric being higher than the second and third length metrics and the third length metric being higher than the second length metric.

Thus, as explained above, a beamforming quality metric may be calculated for each receive channel, for each of a plurality of time-delayed channel signals, at each of a plurality of depths (or depth ranges), and at each transmit event. For a given depth, receive channel, and transmit, a time-delayed channel signal may be selected from among a subset of time-delayed channel signals, where each time-delayed channel signal in the subset of time-delayed channel signals is delayed from an original channel signal using a different beamforming sound speed, and where the original channel signal was received over the given receive channel. The time-delayed channel signal may be selected based on its beamforming quality metric relative to the other beamforming quality metrics calculated for each time-delayed channel signal in the subset of time-delayed channel signals. For example, the selected time-delayed channel signal may have the highest beamforming quality metric of all the time-delayed channel signals in the subset of time-delayed channel signals. In another example, the selected time-delayed channel signal may be a weighted sum (e.g., weighted average) of some or all the time-delayed channel signals in the subset of time-delayed channel signals, where each time-delayed channel signal is weighted based on its respective beamforming quality metric. In some examples, the beamforming quality metric may be a coherence metric that indicates a level of similarity among the time-delayed channel signal under consideration (received over a given receive channel) and one or more adjacent time-delayed channel signals, where the one or more adjacent time-delayed channel signals are time-delayed based on the same beamforming sound speed, at the same depth, and the same transmit as the time-delayed channel signal under consideration, and are received over receive channels adjacent to the given receive channel (e.g., the 1-5 receive channels on either side of the given receive channel). In some examples, the beamforming quality metric may include the coherence metric and a length metric, where the length metric indicates how many contiguous receive channels around the given receive channel also have a coherence metric above a threshold value. In this way, the beamforming quality metric (whether based only on the coherence metric or both the coherence metric and the length metric) may be used to select optimal time-delayed channel signals (whether based on the maximum beamforming quality metric for the subset of time-delayed channel signals or based on the weighted average of the time-delayed channel signals of the subset of time-delayed channel signals).

A technical effect of using a calculated beamforming quality metric to automatically select a time-delayed channel signal independently for each receive channel at each depth in ultrasound image generation is that ultrasound image quality may be improved without operator involvement.

The disclosure also provides support for a method for an ultrasound system including a plurality of ultrasound transducers each coupled to a respective receive channel, comprising: time-delaying a set of ultrasound receive channel signals to form a plurality of time-delayed sets of ultrasound receive channel signals, each time-delayed set of ultrasound receive channel signals time-delayed based on a different beamforming sound speed, calculating a beamforming quality metric for each receive channel and for each time-delayed set of ultrasound receive channel signals, and generating an ultrasound image from ultrasound receive channel signals selected from the plurality of time-delayed sets of ultrasound receive channel signals based on each beamforming quality metric. In a first example of the method, each respective different beamforming sound speed is selected from a set of possible beamforming sound speeds, wherein time-delaying the set of ultrasound receive channel signals to form the plurality of time-delayed sets of ultrasound receive channel signals comprises acquiring and storing in memory the set of ultrasound receive channel signals and time-delaying the set of ultrasound receive channel signals multiple times, each time using a respective different beamforming sound speed, such that a time-delayed set of ultrasound receive channel signals is generated for each beamforming sound speed in the set of possible beamforming sound speeds. In a second example of the method, optionally including the first example, each beamforming quality metric includes a respective coherence metric reflecting a level of coherence among a respective subset of ultrasound receive channel signals. In a third example of the method, optionally including one or both of the first and second examples, calculating the respective coherence metric for each receive channel and for each time-delayed set of ultrasound receive channel signals comprises: for a first time-delayed set of ultrasound receive channel signals time delayed based on a first beamforming sound speed, calculating a first coherence metric for each receive channel based on a respective subset of the first time-delayed set of ultrasound receive channel signals, each respective subset received over that receive channel and one or more adjacent receive channels, and repeating the coherence metric calculation for each receive channel for each remaining time-delayed set of ultrasound receive channel signals such that a coherence metric is calculated for each receive channel at each different beamforming sound speed. In a fourth example of the method, optionally including one or more or each of the first through third examples, each beamforming quality metric further includes a respective length metric that reflects, for that receive channel, how many additional receive channels contiguous with that receive channel have a coherence metric above a threshold value. In a fifth example of the method, optionally including one or more or each of the first through fourth examples, generating an ultrasound image from the selected ultrasound receive channel signals comprises: for each receive channel, calculating a weighted sum of each time-delayed ultrasound receive channel signal received over that receive channel, where each time-delayed ultrasound receive channel signal is weighted based on a corresponding beamforming quality metric calculated for that receive channel and time-delayed ultrasound receive channel signal, and generating the ultrasound image from each weighted sum. In a sixth example of the method, optionally including one or more or each of the first through fifth examples, generating an ultrasound image from the selected ultrasound receive channel signals comprises: for each receive channel, selecting the time-delayed ultrasound receive channel signal received over that receive channel that has the highest beamforming quality metric, and generating the ultrasound image from the selected time-delayed ultrasound receive channel signals. In a seventh example of the method, optionally including one or more or each of the first through sixth examples, a beamforming quality metric is calculated for each receive channel at each depth of a plurality of depths, for each beamforming sound speed. In an eighth example of the method, optionally including one or more or each of the first through seventh examples, a beamforming quality metric is calculated for each receive channel at each of a plurality of overlapping or non-overlapping depth ranges, for each beamforming sound speed. In a ninth example of the method, optionally including one or more or each of the first through eighth examples, the set of ultrasound receive channel signals is a first set of ultrasound receive channel signals obtained upon a transmit event, and further comprising repeating the time-delaying, beamforming quality metric calculation, and ultrasound receive channel signal selection for each additional set of ultrasound receive channel signals obtained upon each additional transmit event.

The disclosure also provides support for a system, comprising: a plurality of ultrasound transducers configured to transmit and receive ultrasound signals, a memory storing instructions, and a processor configured to execute the instructions to: acquire, via the plurality of ultrasound transducers, a set of ultrasound receive channel signals, calculate a respective set of beamforming quality metrics for each of a plurality of time-delayed sets of ultrasound receive channel signals, where each time-delayed set of ultrasound receive channel signals is time-delayed from the set of ultrasound receive channel signals based on a different beamforming sound speed, generate an ultrasound image from selected time-delayed ultrasound receive channel signals of the plurality of time-delayed ultrasound receive channel signals based on each respective set of beamforming quality metrics. In a first example of the system, the set of ultrasound receive channel signals is received via a set of receive channels each coupled to an ultrasound transducer of the plurality of ultrasound transducers, and wherein each beamforming quality metric includes a measure of similarity among selected time-delayed ultrasound receive channel signals. In a second example of the system, optionally including the first example, each beamforming quality metric includes a respective coherence metric for each receive channel, each coherence metric comprising an absolute value of summed time-delayed channel signals for a respective subset of receive channels to a sum of absolute values of time-delayed channel signals for the respective subset of receive channels, the respective subset of receive channels including that receive channel and one or more adjacent receive channels. In a third example of the system, optionally including one or both of the first and second examples, generating an ultrasound image from the selected time-delayed ultrasound receive channel signals comprises: for each receive channel, calculating a weighted sum of each time-delayed ultrasound receive channel signal received over that receive channel, where each time-delayed ultrasound receive channel signal is weighted based on a corresponding beamforming quality metric calculated for that receive channel and time-delayed ultrasound receive channel signal, and generating the ultrasound image from each weighted sum. In a fourth example of the system, optionally including one or more or each of the first through third examples, generating an ultrasound image from the selected time-delayed ultrasound receive channel signals comprises: for each receive channel, selecting the time-delayed ultrasound receive channel signal received over that receive channel that has the highest beamforming quality metric, and generating the ultrasound image from the selected time-delayed ultrasound receive channel signals. In a fifth example of the system, optionally including one or more or each of the first through fourth examples, a respective set of beamforming quality metrics is calculated at each depth of a plurality of depths for each of the plurality of time-delayed sets of ultrasound receive channel signals.

The disclosure also provides support for a method, comprising, generating an ultrasound image from a selected set of time-delayed receive channel signals, including, for each time-delayed receive channel signal of the selected set, selecting that time-delayed receive channel signal independently from among a plurality of possible time-delayed receive channel signals based on a set of beamforming quality metrics calculated for each time-delayed receive channel signal of the plurality of possible time-delayed receive channel signals. In a first example of the method, the plurality of possible time-delayed receive channel signals is generated by acquiring and storing in memory an original set of receive channel signals and time-delaying the original set of receive channel signals multiple times, each time using a respective different beamforming sound speed, such that a time-delayed set of receive channel signals is generated for each beamforming sound speed in the set of possible beamforming sound speeds. In a second example of the method, optionally including the first example, each receive channel signal of the original set of receive channel signals is received over a separate receive channel, wherein each beamforming quality metric of the set of beamforming quality metrics is calculated for a respective receive channel by calculating a coherence metric over a moving window of time-delayed receive channel signals, the moving window centered over that receive channel. In a third example of the method, optionally including one or both of the first and second examples, selecting that time-delayed receive channel signal independently from among the plurality of possible time-delayed receive channel signals based on the set of beamforming quality metrics comprises, for a given receive channel, selecting a time-delayed receive channel signal that has the highest beamforming quality metric of all time-delayed receive channel signals received over that receive channel for a given depth and transmit event.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for an ultrasound system including a plurality of ultrasound transducers each coupled to a respective receive channel, comprising:
    time-delaying a set of ultrasound receive channel signals to form a plurality of time-delayed sets of ultrasound receive channel signals, each time-delayed set of ultrasound receive channel signals time-delayed based on a different beamforming sound speed;
    calculating a beamforming quality metric for each receive channel and for each time-delayed set of ultrasound receive channel signals; and
    generating an ultrasound image from ultrasound receive channel signals selected from the plurality of time-delayed sets of ultrasound receive channel signals based on each beamforming quality metric.

2. The method of claim 1, wherein each respective different beamforming sound speed is selected from a set of possible beamforming sound speeds, wherein time-delaying the set of ultrasound receive channel signals to form the plurality of time-delayed sets of ultrasound receive channel signals comprises acquiring and storing in memory the set of ultrasound receive channel signals and time-delaying the set of ultrasound receive channel signals multiple times, each time using a respective different beamforming sound speed, such that a time-delayed set of ultrasound receive channel signals is generated for each beamforming sound speed in the set of possible beamforming sound speeds.

3. The method of claim 1, wherein each beamforming quality metric includes a respective coherence metric reflecting a level of coherence among a respective subset of ultrasound receive channel signals.

4. The method of claim 3, wherein calculating the respective coherence metric for each receive channel and for each time-delayed set of ultrasound receive channel signals comprises:
    for a first time-delayed set of ultrasound receive channel signals time delayed based on a first beamforming sound speed, calculating a first coherence metric for each receive channel based on a respective subset of the first time-delayed set of ultrasound receive channel signals, each respective subset received over that receive channel and one or more adjacent receive channels; and
    repeating the coherence metric calculation for each receive channel for each remaining time-delayed set of ultrasound receive channel signals such that a coherence metric is calculated for each receive channel at each different beamforming sound speed.

5. The method of claim 3, wherein each beamforming quality metric further includes a respective length metric that reflects, for that receive channel, how many additional receive channels contiguous with that receive channel have a coherence metric above a threshold value.

6. The method of claim 1, wherein generating an ultrasound image from the selected ultrasound receive channel signals comprises:
    for each receive channel, calculating a weighted sum of each time-delayed ultrasound receive channel signal received over that receive channel, where each time-delayed ultrasound receive channel signal is weighted based on a corresponding beamforming quality metric calculated for that receive channel and time-delayed ultrasound receive channel signal; and
    generating the ultrasound image from each weighted sum.

7. The method of claim 1, wherein generating an ultrasound image from the selected ultrasound receive channel signals comprises:
    for each receive channel, selecting the time-delayed ultrasound receive channel signal received over that receive channel that has the highest beamforming quality metric; and
    generating the ultrasound image from the selected time-delayed ultrasound receive channel signals.

8. The method of claim 1, wherein a beamforming quality metric is calculated for each receive channel at each depth of a plurality of depths, for each beamforming sound speed.

9. The method of claim 8, further comprising combining the plurality of depths into a plurality of ranges of depths and calculating a beamforming quality metric for each of the plurality of ranges of depths.

10. The method of claim 8, further comprising calculating a first beamforming quality metric for a first depth and applying the calculated first beamforming quality metric to one or more depths above and/or below the first depth.

11. The method of claim 10, wherein the one or more depths above and/or below the first depth are each at least two depths above or below the first depth.

12. The method of claim 1, wherein a beamforming quality metric is calculated for each receive channel at each of a plurality of overlapping or non-overlapping depth ranges, for each beamforming sound speed.

13. The method of claim 1, wherein the set of ultrasound receive channel signals is a first set of ultrasound receive channel signals obtained upon a transmit event, and further comprising repeating the time-delaying, beamforming quality metric calculation, and ultrasound receive channel signal selection for each additional set of ultrasound receive channel signals obtained upon each additional transmit event.

14. A system, comprising:
    a plurality of ultrasound transducers configured to transmit and receive ultrasound signals;
    a memory storing instructions; and
    a processor configured to execute the instructions to:
        acquire, via the plurality of ultrasound transducers, a set of ultrasound receive channel signals;
        calculate a respective set of beamforming quality metrics for each of a plurality of time-delayed sets of ultrasound receive channel signals, where each time-delayed set of ultrasound receive channel signals is time-delayed from the set of ultrasound receive channel signals based on a different beamforming sound speed;
        generate an ultrasound image from selected time-delayed ultrasound receive channel signals of the plurality of time-delayed ultrasound receive channel signals based on each respective set of beamforming quality metrics.

15. The system of claim 14, wherein the set of ultrasound receive channel signals is received via a set of receive channels each coupled to an ultrasound transducer of the plurality of ultrasound transducers, and wherein each beamforming quality metric includes a measure of similarity among selected time-delayed ultrasound receive channel signals.

16. The system of claim 15, wherein each beamforming quality metric includes a respective coherence metric for each receive channel, each coherence metric comprising an absolute value of summed time-delayed channel signals for a respective subset of receive channels to a sum of absolute values of time-delayed channel signals for the respective subset of receive channels, the respective subset of receive channels including that receive channel and one or more adjacent receive channels.

17. The system of claim 14, wherein generating an ultrasound image from the selected time-delayed ultrasound receive channel signals comprises:
for each receive channel, calculating a weighted sum of each time-delayed ultrasound receive channel signal received over that receive channel, where each time-delayed ultrasound receive channel signal is weighted based on a corresponding beamforming quality metric calculated for that receive channel and time-delayed ultrasound receive channel signal; and
generating the ultrasound image from each weighted sum.

18. The system of claim 14, wherein generating an ultrasound image from the selected time-delayed ultrasound receive channel signals comprises:
for each receive channel, selecting the time-delayed ultrasound receive channel signal received over that receive channel that has the highest beamforming quality metric; and
generating the ultrasound image from the selected time-delayed ultrasound receive channel signals.

19. The system of claim 14, wherein a respective set of beamforming quality metrics is calculated at each depth of a plurality of depths for each of the plurality of time-delayed sets of ultrasound receive channel signals.

20. A method, comprising;
generating an ultrasound image from a selected set of time-delayed receive channel signals, including, for each time-delayed receive channel signal of the selected set, selecting that time-delayed receive channel signal independently from among a plurality of possible time-delayed receive channel signals based on a set of beamforming quality metrics calculated for each time-delayed receive channel signal of the plurality of possible time-delayed receive channel signals.

21. The method of claim 20, wherein the plurality of possible time-delayed receive channel signals is generated by acquiring and storing in memory an original set of receive channel signals and time-delaying the original set of receive channel signals multiple times, each time using a respective different beamforming sound speed, such that a time-delayed set of receive channel signals is generated for each beamforming sound speed in the set of possible beamforming sound speeds.

22. The method of claim 21, wherein each receive channel signal of the original set of receive channel signals is received over a separate receive channel, wherein each beamforming quality metric of the set of beamforming quality metrics is calculated for a respective receive channel by calculating a coherence metric over a moving window of time-delayed receive channel signals, the moving window centered over that receive channel.

23. The method of claim 22, wherein selecting that time-delayed receive channel signal independently from among the plurality of possible time-delayed receive channel signals based on the set of beamforming quality metrics comprises, for a given receive channel, selecting a time-delayed receive channel signal that has the highest beamforming quality metric of all time-delayed receive channel signals received over that receive channel for a given depth and transmit event.

* * * * *